United States Patent
Schrock et al.

(10) Patent No.: US 10,874,862 B2
(45) Date of Patent: Dec. 29, 2020

(54) CIRCUIT CONFIGURATION BASED ON DEPOPULATED PINS

(71) Applicant: Medtronic, Inc., Minneapolis, MN (US)

(72) Inventors: Anthony W. Schrock, Ham Lake, MN (US); Michael L. Hudziak, Stillwater, MN (US); James J. St. Martin, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 359 days.

(21) Appl. No.: 15/900,837

(22) Filed: Feb. 21, 2018

(65) Prior Publication Data
US 2018/0250515 A1    Sep. 6, 2018

Related U.S. Application Data

(60) Provisional application No. 62/466,840, filed on Mar. 3, 2017.

(51) Int. Cl.
| | |
|---|---|
| *A61N 1/37* | (2006.01) |
| *A61N 1/372* | (2006.01) |
| *A61N 1/39* | (2006.01) |
| *A61N 1/02* | (2006.01) |
| *A61N 1/368* | (2006.01) |
| *A61N 1/365* | (2006.01) |
| *A61N 1/05* | (2006.01) |

(52) U.S. Cl.
CPC ............. *A61N 1/371* (2013.01); *A61N 1/025* (2013.01); *A61N 1/368* (2013.01); *A61N 1/37217* (2013.01); *A61N 1/3956* (2013.01); *A61N 1/0563* (2013.01); *A61N 1/365* (2013.01)

(58) Field of Classification Search
CPC ........ A61N 1/371; A61N 1/368; A61N 1/025; A61N 1/3956; A61N 1/37217; A61N 1/0563; A61N 1/365
See application file for complete search history.

(56) References Cited

U.S. PATENT DOCUMENTS

| | | |
|---|---|---|
| 4,928,023 A | 5/1990 | Marshall |
| 5,319,260 A | 6/1994 | Wanlas |
| 5,436,584 A | 7/1995 | Bodas et al. |

(Continued)

OTHER PUBLICATIONS (PCT/US2018/020633) PCT Notification of Transmittal of the International Search Report and the Written Opinion of the International Searching Authority, dated May 28, 2018, 8 pages.

*Primary Examiner* — Amanda K Hulbert
*Assistant Examiner* — Natasha Patel
(74) *Attorney, Agent, or Firm* — Shumaker & Sieffert, P.A.

(57) ABSTRACT

Examples are described for configuring cardiac pacing circuitry of an implantable medical device. Circuitry that is configurable to control delivery of therapy or sense signals in accordance with a plurality of vectors may determine that one or more pins, for therapy delivery or sensing in accordance with a first subset of vectors of the plurality of vectors, are in an electrically floating state. Circuitry may selectively close one or more switches to couple at least a subset of the one or more pins to one or more set voltage levels, and deliver therapy in accordance with a vector of a second subset of vectors of the plurality of vectors, wherein the second subset of vectors is different than the first subset of vectors.

29 Claims, 6 Drawing Sheets

(56) References Cited

U.S. PATENT DOCUMENTS

| | | | |
|---|---|---|---|
| 5,546,021 | A | 8/1996 | Bizuneh et al. |
| 7,184,833 | B2 | 2/2007 | Ganion et al. |
| 7,876,129 | B2 | 1/2011 | Lu et al. |
| 2006/0247739 | A1 | 11/2006 | Wahlstrand et al. |
| 2010/0114248 | A1* | 5/2010 | Donofrio ............... A61N 1/025 607/60 |
| 2011/0264171 | A1 | 10/2011 | Torgerson |
| 2016/0339248 | A1 | 11/2016 | Schrock et al. |

* cited by examiner

CIRCUIT CONFIGURATION BASED ON DEPOPULATED PINS

CROSS-REFERENCE TO RELATED APPLICATIONS

This application claims the benefit of U.S. provisional application Ser. No. 62/466,840, filed Mar. 3, 2017, the entire content of which is incorporated by reference herein.

TECHNICAL FIELD

This disclosure relates to implantable medical devices, and more particularly, to implantable medical devices that deliver cardiac pacing.

BACKGROUND

A wide variety of implantable medical devices for delivering a therapy or monitoring a physiologic condition have been clinically implanted or proposed for clinical implantation in patients. In some cases, implantable medical devices (IMD) deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for sensing or delivery of stimulation. For example, electrodes or sensors may be carried at a distal portion of the lead. A proximal portion of the lead that may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation, via electrodes of one or more implantable leads. In some cases, such an implantable medical device may sense for intrinsic depolarizations of the heart, and control the delivery of such signals to the heart based on the sensing. When an abnormal rhythm is detected, which may be bradycardia, tachycardia or fibrillation, an appropriate electrical signal or signals may be delivered to restore the normal rhythm. For example, in some cases, an implantable medical device may deliver pacing, cardioversion or defibrillation signals to the heart of the patient upon detecting ventricular tachycardia, and deliver defibrillation electrical signals to a patient's heart upon detecting ventricular fibrillation. Pacing signals typically have a lower energy than the cardioversion or defibrillation signals.

SUMMARY

In general, this disclosure describes techniques for setting voltage levels for pins that are not to be used for delivering cardiac pacing therapy in an implantable medical device (IMD). Based on types of therapy to be delivered and/or types of leads coupled to the IMD, certain pins of an integrated circuit (IC) chip may not be coupled to therapy delivering electrodes, and may be in an electrically floating state (e.g., not at a fixed voltage level). The techniques described in this disclosure describe example ways in which to set the voltage level of these pins by selectively closing switches that are internal to the IC chip, and ensuring the closing of such switches does not result in determination that a pacing therapy can be delivered via these pins.

In one example, the disclosure is directed to a method of configuring cardiac pacing circuitry of an implantable medical device, the method comprising determining, with processing circuitry that is configurable to control deliver of therapy or sense signals in accordance with a plurality of vectors, that one or more pins, for therapy delivery or sensing in accordance with a first subset of vectors of the plurality of vectors, are in an electrically floating state, selectively closing one or more switches to couple at least a subset of the one or more pins to one or more set voltage levels, and delivering therapy in accordance with a vector of a second subset of vectors of the plurality of vectors, wherein the second subset of vectors is different than the first subset of vectors.

In another example, the disclosure is directed to an implantable medical device (IMD), the device comprising an integrated circuit (IC) chip comprising a plurality of switches, and a plurality of pins. The device comprising circuitry that is configurable to control deliver of therapy or sense signals in accordance with a plurality of vectors, wherein the circuitry is configured to determine that one or more pins of the plurality of pins, for therapy delivery or sensing in accordance with a first subset of vectors of the plurality of vectors, are in an electrically floating state, selectively close one or more switches of the plurality of switches to couple at least a subset of the one or more pins to one or more set voltage levels, and cause the IMD to deliver therapy in accordance with a vector of a second subset of vectors of the plurality of vectors, wherein the second subset of vectors is different than the first subset of vectors.

In another example, the disclosure is directed to an implantable medical device (IMD), the device comprising circuitry that is configurable to control delivery of therapy or sense signals in accordance with a plurality of vectors, wherein the circuitry comprises means for determining that one or more pins, for therapy delivery or sensing in accordance with a first subset of vectors of the plurality of vectors, are in an electrically floating state, means for selectively closing one or more switches to couple at least a subset of the one or more pins to one or more set voltage levels, and means for causing delivery of therapy in accordance with a vector of a second subset of vectors of the plurality of vectors, wherein the second subset of vectors is different than the first subset of vectors.

In another example, the disclosure is directed to computer-readable storage medium storing instruction thereon that when executed cause circuitry that is configurable to control delivery of therapy or sense signals in accordance with a plurality of vectors to determine that one or more pins, for therapy delivery or sensing in accordance with a first subset of vectors of the plurality of vectors, are in an electrically floating state, selectively close one or more switches to couple at least a subset of the one or more pins to one or more set voltage levels, and cause delivery of therapy in accordance with a vector of a second subset of vectors of the plurality of vectors, wherein the second subset of vectors is different than the first subset of vectors.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
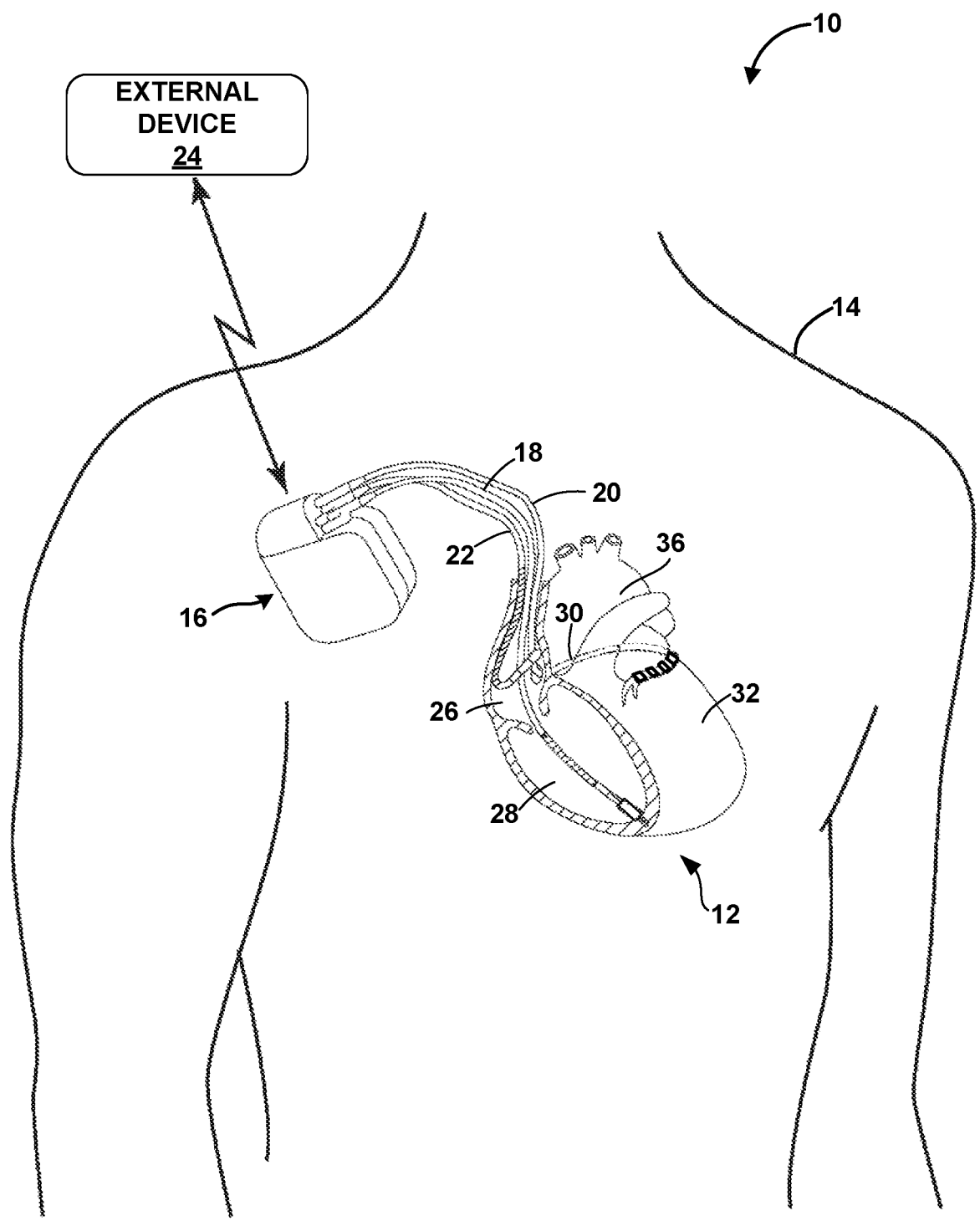
FIG. 1 is a conceptual diagram illustrating an example system that may be used to provide therapy to and/or monitor a heart of a patient.

This disclosure describes techniques for coupling pins of an integrated circuit (IC) chip of an implantable medical device (IMD) that are not used for delivery of cardiac pacing therapy to a set voltage level. For example, the IC chip may be configurable to deliver cardiac pacing therapy in accordance with a plurality of vectors, where a vector refers a combination of electrodes through which the current of the therapy travels. To provide the therapy in accordance with the plurality of vectors, the IC chip may include therapy delivery pins that couple to various electrodes on one or more leads and/or on a housing of the IMD, as well as pins coupled to capacitors used to deliver the charge.

However, not all vectors may be available or needed in all cases. For example, the IC chip may be configurable for different device configurations or prescriptions. In other words, the same IC chip may be utilized for single chamber cardiac devices that provide electrical stimulation to single heart chamber, dual chamber cardiac devices that provide electrical stimulation to two heart chambers (e.g., atrial and ventricular stimulation), or cardiac resynchronization therapy (CRT) devices that provide electrical stimulation to two or three chambers of the heart (e.g., both ventricles as well as possibly the atrium). For example, the IC chip may be configured for full three chamber with quadripolar left ventricular implementation which supports vectors for atrial therapy delivery, right ventricular therapy delivery, as well as vectors provided by four left ventricular electrodes for left ventricular therapy delivery.

Moreover, within each of these various devices, several possible electrode vectors may be available for pacing and/or sensing as will be described in further detail herein. Because the IC chip may be used for such a wide variety of device configurations, based on patient need, the IMD implanted in the patient may be configured to deliver therapy in accordance with only a subset of the plurality of vectors that the IC chip is configurable to deliver. As another example, the IC chip may be configurable for full quadripolar implementation which supports vectors for atrial therapy delivery, right ventricular therapy delivery, as well as four vectors for left ventricular therapy delivery. However, based on the number of leads and/or the number of electrodes on the lead(s) that are to be implanted in the patient, the IMD that couples to the lead may need to delivery therapy in accordance with only a subset of the plurality of vectors that the IC chip is configurable to deliver, e.g., as would be the case in a single or dual chamber device configuration.

Accordingly, although the IC chip is configurable to deliver therapy in accordance with a plurality of vectors, there may be a first subset of vectors of the plurality of vectors, and the IC chip is not to deliver therapy in accordance with the first subset of vectors (e.g., based on patient need). There is also a second subset of vectors of the plurality of vectors, where the IC chip may deliver therapy in accordance with one or more vectors of the second subset of vectors.

The first subset of vectors also includes sensing vectors in addition to therapy vectors, and similarly, the second subset of vectors include sensing vectors in addition to therapy vectors. A sensing vector refers to a vector used for sensing signals of the patient, such as signals that indicate whether recapture occurred. In this disclosure, the first subset of vectors and the second subset of vectors should be understood as including therapy vectors, sensing vectors, and/or a combination of therapy vectors and sensing vectors.

The pins that would have been used to deliver therapy or sense signals in accordance with first subset of vectors may not be needed. Accordingly, external components that couple to these pins may be depopulated (e.g., not connected or placed) in the IMD. Whether the external components are depopulated or not, one potential issue is that these unused pins for the first subset of vectors are in an electrically floating state. In the electrically floating state, the voltage level at these pins can vary. Because the pins are in the electrically floating state, electrical noise may be carried by these pins into the IC chip (e.g., the pins may function as an electrical input into the IC chip for the electrical noise).

One example way to limit electrical noise from being carried into the IC chip is to couple the unused pins (e.g., those for the first subset of vectors) to a set voltage using external components. For example, each of the unused pins may be directly connected to the supply voltage or to the ground potential through external power and ground pads, or connected to the supply voltage or around potential through a coupling resistor.

Using external power and ground pads and/or using additional coupling resistors increases real estate on the circuit board because traces, pads, and components needed for the connection to the supply voltage or ground, and increase cost because of the additional components. Using external power and ground pads and/or using additional coupling resistors may also potentially decrease reliability because the external components may break (e.g., pads may become disconnected from the circuit board, the resistor may break or become disconnected, etc.).

The example techniques described in the disclosure include techniques to determine that one or more pins, for therapy delivery or sensing signals in accordance with a first subset of vectors of the plurality of vectors, are in an electrically floating state. Processing circuitry may selectively close one or more switches to couple at least a subset of the one or more pins that are in the electrically floating state to one or more set voltage levels (e.g., supply voltage, ground potential, or some intermediate voltage set by a voltage driver). In general, the processing circuitry may utilize switches (e.g., internal to or possibly external to) the IC chip instead of or in addition to external components to ensure that the pins that are not used for therapy delivery or sensing in accordance with the vector(s) for which the IC chip is configured are at a set voltage level.

The processing circuitry may then cause the IMD to deliver therapy in accordance with a vector for which the processing circuitry is configured. In some cases, one of the pins that is not coupled to additional external components (e.g., the components to which it would couple are depopulated) may be coupled to the ground potential. This may cause the processing circuitry to determine that a valid vector for pacing is present because the processing circuitry may determine that there is a path to ground for the electrical pacing therapy that the IMD delivers. In response, the processing circuitry may cause the IMD to deliver therapy.

However, although one of the pins that is not coupled to additional external components is coupled to ground, this pin does not provide a valid return path for the current from the delivered therapy because the pin is not connected to any electrode or case through which the current can return to ground. In some examples, the processing circuitry may not deliver the therapy until after determining that at least one pin, other than the pin that is connected to ground but does not provide a valid current path, is also connected to the ground potential.

As one example, this disclosure describes digital circuitry that masks the fact that the pin not used for therapy delivery or sensing is connected to the ground potential. Accordingly, digital circuitry may ensure that the therapy is not delivered until there is another pin that is connected to the ground potential. There may be various ways to ensure that there is a valid ground connection (e.g., at least one pin other than pins not used for therapy delivery are connected to the ground potential), and the use of the digital circuitry is provided as one example. For instance, confirmation of a valid ground connection may be performed by processing circuitry itself based on firmware or software executing on the processing circuitry.

FIG. 1 is a conceptual diagram illustrating an example system 10 that may be used to monitor and/or provide therapy to heart 12 of patient 14. Patient 14 ordinarily, but not necessarily, will be a human. System 10 includes IMD 16, which is coupled to leads 18, 20, and 22, and external device 24. IMD 16 may be, for example, an implantable pacemaker, cardioverter, and/or defibrillator that provides electrical signals to heart 12 via electrodes coupled to one or more of leads 18, 20, and 22. In accordance with this disclosure, IMD 16 may deliver A (Atrial), RV (Right Ventricular), or four different LV (Left Ventricular) pacing pulses via a plurality of pacing vectors that include one or more electrodes in leads 18, 20, and 22.

However, other example systems 10 that include IMDs 16 that are not configured to couple to one or more of leads 18, 20, and 22, or configured to couple to leads with fewer electrodes than are provided by leads 18, 20, and 22, may be implanted in patient 14. Accordingly, although processing circuitry within IMD 16 may be configurable to deliver therapy via a plurality of vectors for A, RV, or LV pacing pulses, a particular configuration of IMD 16 may only deliver therapy in accordance with a subset of the vectors. Also, in some examples, patient 14 may not need therapy in accordance with all of the different types of pacing pulses, and in such examples, IMD 16 may only deliver therapy in accordance with a subset of the vectors.

Leads 18, 20, 22 extend into the heart 12 of patient 16 to sense electrical activity of heart 12 and/or deliver electrical stimulation to heart 12. In the example shown in FIG. 1, RV lead 18 extends through one or more veins (not shown), the superior vena cava (not shown), and right atrium 26, and into right ventricle 28. LV coronary sinus lead 20 extends through one or more veins, the vena cava, right atrium 26, and into the coronary sinus 30 to a region adjacent to the free wall of left ventricle 32 of heart 12. RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

The placement of IMD 16 and the placement of leads 18, 20, 22 is provided as one example. In some examples, IMD 16 may be implanted subcutaneously or submuscularly on a side of patient 14 (e.g., left side) and above the ribcage. Leads 18, 20, 22, usable for defibrillation and/or pacing, may be implanted at least partially in a substernal location (e.g., between the ribcage and/or sternum and heart 12). Other placement locations for IMD 16 and placement of leads 18, 20, 22 or other lead types coupled to IMD 16 are possible.

In some examples, external device 24 may be a handheld computing device or a computer workstation. A user, such as a physician, technician, or other clinician, may interact with external device 24 to communicate with IMD 16. For example, the user may interact with external device 24 to retrieve physiological or diagnostic information from IMD 16. A user may also interact with external device 24 to program IMD 16, e.g., select values for operational parameters of the IMD.

For example, the user may use external device 24 to retrieve information from IMD 16 regarding the rhythm of heart 12, trends therein over time, or arrhythmic episodes. As another example, the user may use external device 24 to retrieve information from IMD 16 regarding other sensed physiological parameters of patient 14, such as intracardiac or intravascular pressure, activity, posture, respiration, or thoracic impedance. As another example, the user may use external device 24 to retrieve information from IMD 16 regarding the performance or integrity of IMD 16 or other components of system 10, such as leads 18, 20 and 22, or a power source of IMD 16. The user may use external device 24 to program a therapy progression, select electrodes used to deliver defibrillation pulses, select waveforms for the defibrillation pulse, or select or configure a fibrillation detection algorithm for IMD 16. The user may also use external device 24 to program aspects of other therapies provided by IMD 14, such as cardioversion or pacing therapies.

IMD 16 and external device 24 may communicate via wireless communication using any techniques known in the art. Examples of communication techniques may include, for example, low frequency or radiofrequency (RF) telemetry, but other techniques are also contemplated. In some examples, external device 24 may include a programming head that may be placed proximate to the patient's body near the IMD 16 implant site in order to improve the quality or security of communication between IMD 16 and external device 24.

IMD 16 may include one or more integrated circuit (IC) chips. For ease of illustration and description, the techniques are described with respect to one IC chip. However, the techniques described in this disclosure are also applicable to examples whether IMD 16 includes a plurality of IC chips, such as where the example components described in this disclosure are spread across different IC chips.

The IC chip includes a plurality of pins that form as connection points between components internal to the IC chip and components external to the IC chip. As an example, to deliver therapy, processing circuitry of the IC chip may store charge on a capacitor. This capacitor may be external to the processing circuitry, and therefore, the IC chip may include two pins that couple the IC chip to the external capacitor (e.g., one pin for each side of the capacitor). The IC chip may include similar pins that couple to external capacitors for the different vectors for delivery of the pacing pulses (e.g., A, RV, or the four LV).

Also, the IC chip may include pins from which the pacing pulses output the IC chip and are delivered via the electrodes of leads 18, 20, and 22, and pins from which the current of the pacing pulses returns. To deliver the pacing pulses, an external capacitor may be coupled to one or more pins (cathodes), and one or more other pins (anodes) are used to return the current. For some vectors, an external capacitor may be used with different switching matrices to control the delivery of the current.

In examples where there is a first subset of vectors of the plurality of vectors in accordance with which IMD 16 does not need to delivery therapy or sense (or generally any pins for vectors that are not connected to an external electrode or component), the external capacitors for pins that are used to delivery therapy or sense in accordance with only the first subset of vectors may not need to included (e.g., these capacitors can be depopulated). The removal of these capacitors (or even if the capacitors were present) may cause the pins for the first subset of vectors to be in a floating electrical state (e.g., not set to any reference voltage such as the supply voltage or ground). Because the pins for the subset of vectors are in the floating electrical state, the voltage at the pins can vary, and the pins may function as an input for noise into the processing circuitry.

One way to limit the noise may be to use external components that couple the pins for the first subset of vectors to a set voltage level (e.g., via direct connection or resistive connection). However, the use of external components may result in inefficient use of circuit board space, increase in cost, and decrease in reliability.

In the techniques described in this disclosure, the IC chip may include a plurality of switches that selectively couple pins used for the first subset of vectors (e.g., vectors that are not needed for providing therapy to the patient or sensing signals in the patient) to a set voltage level. For example, the processing circuitry may selectively close one or more switches to couple at least a subset of the pins, for therapy delivery in accordance with the first subset of vectors, that are in an electrically floating state to one or more set voltage levels. The processing circuitry may then cause therapy to be delivered or signals to be sensed in accordance with a vector of a second subset of vectors via one or more pins for therapy delivery or signal sensing in accordance with the vector of the second subset of vectors. The one or more pins for therapy delivery or signal sensing in accordance with the vector of the second subset of vectors may not be in an electrically floating state prior to therapy delivery and subsequent to therapy delivery, or prior to sensing signals and subsequent to sensing signals.

To deliver pacing therapy, the processing circuitry may ensure that a valid therapy path exists (e.g., a full current path from power to ground of IMD 16). In some cases, the switches may couple one or more pins, for therapy delivery in accordance with the first subset of vectors, to a ground potential. It may be possible that the processing circuitry determines that a valid therapy path exists because one or more pins, for therapy delivery in accordance with the first subset of vectors, are coupled to the ground potential. However, there may not be a valid therapy path because these pins are not connected to any external components, and therefore, may not be able to receive the current from the pacing pulse.

In some examples, the processing circuitry may ensure that at least one pin, other than pins for therapy delivery in accordance with the first subset of vectors, is coupled to the ground potential. As one example, digital circuitry may mask information indicating that one or more pins for therapy delivery in accordance with the first subset of vectors are coupled to ground as part of the determination of whether a valid therapy path exists. After making the determination, the processing circuitry may deliver the therapy. Other techniques, in addition to or instead of the use of digital circuitry, may be used to ensure that at least one pin, other than pins for therapy delivery in accordance with the first subset of vectors, is coupled to the ground potential.

Figure 2:
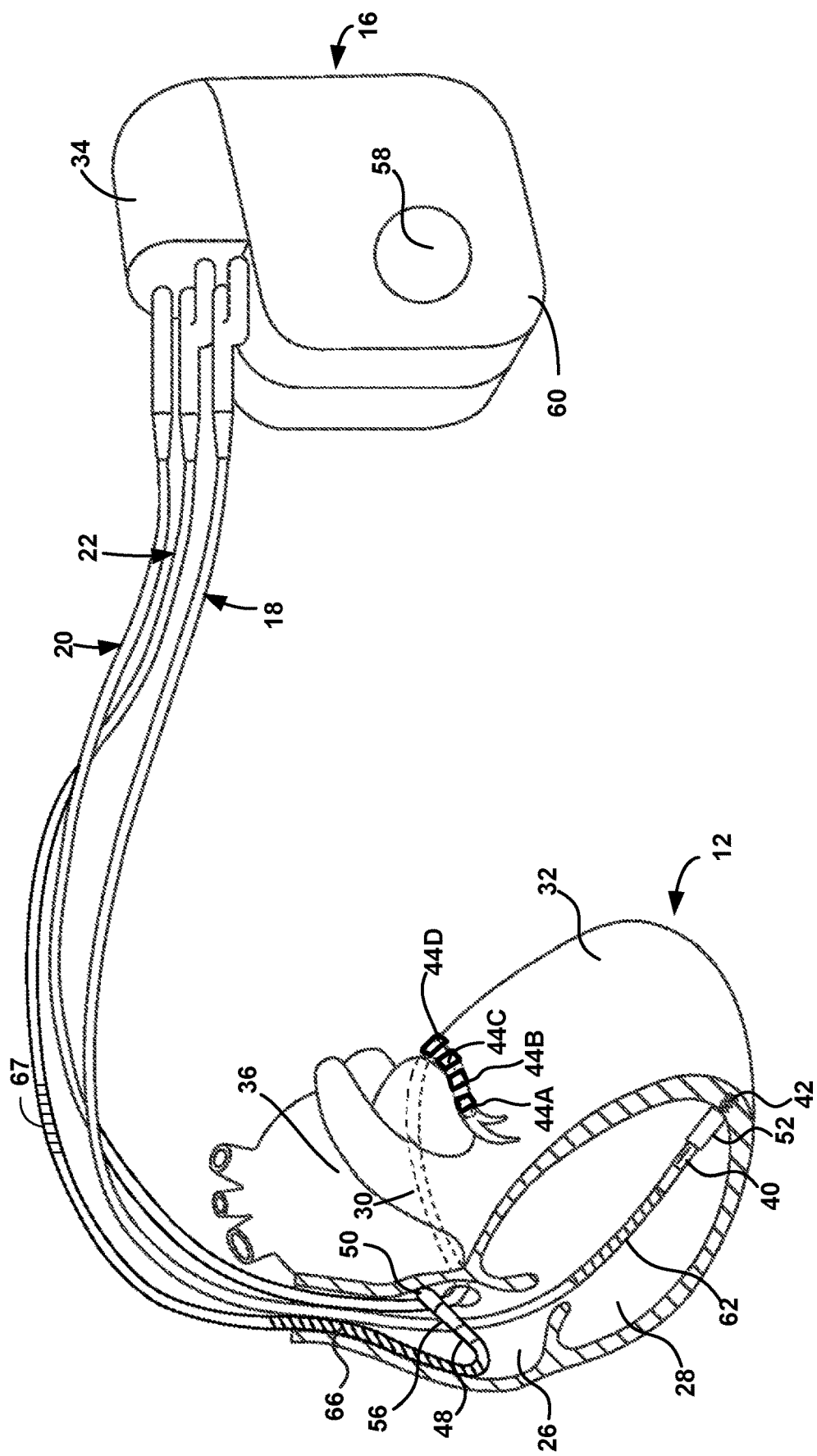
FIG. 2 is a conceptual diagram illustrating the example implantable medical device (IMD) and the leads of the system shown in FIG. 1 in greater detail.

FIG. 2 is a conceptual diagram illustrating IMD 16 and leads 18, 20, and 22 of therapy system 10 in greater detail. Leads 18, 20, 22 may be electrically coupled to a signal generation circuitry and a sensing circuitry of IMD 16 via connector block 34. Although leads 18, 20, and 22 are illustrated, patient 14, based on the type of therapy that should be delivered, may be implanted with fewer or more than all of these example leads, or may be implanted with different lead types. Accordingly, although IMD 16 and its processing circuitry may be configurable to deliver therapy in accordance with a plurality of vectors, IMD 16 and its processing circuitry may be configured to deliver therapy in accordance with a subset of vectors of the plurality of vectors.

Each of the leads 18, 20, 22 includes an elongated insulative lead body carrying one or more conductors. Bipolar electrodes 40 and 42 are located adjacent to a distal end of lead 18 and bipolar electrodes 48 and 50 are located adjacent to a distal end of lead 22. In some example configurations, lead 20 may be a quadripolar lead and, as such, include four electrodes, namely electrodes 44A-44D, which are located adjacent to a distal end of lead 20. Electrodes 40, 44A-44D, and 48 may take the form of ring electrodes, and electrodes 42 and 50 may take the form of extendable helix tip electrodes mounted retractably within insulative electrode heads 52 and 56, respectively.

Leads 18 and 22 also include elongated intracardiac electrodes 62 and 66 respectively, which may take the form of a coil. In addition, one of leads 18, 20, 22, e.g., lead 22 as seen in FIG. 2, may include a superior vena cava (SVC) coil 67 for delivery of electrical stimulation, e.g., transvenous defibrillation. For example, lead 22 may be inserted through the superior vena cava and SVC coil 67 may be placed, for example, at the right atrial/SVC junction (low SVC) or in the left subclavian vein (high SVC). Each of the electrodes 40, 42, 44A-44D, 48, 50, 62, 66 and 67 may be electrically coupled to a respective one of the conductors within the lead body of its associated lead 18, 20, 22, and thereby individually coupled to the signal generation circuitry and sensing circuitry of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 44A-44D, 48, 50, 58, 62, 66 and 67. The electrical signals are conducted to IMD 16 via the respective leads 18, 20, 22, or in the case of housing electrode 58, a conductor coupled to the housing electrode. IMD 16 may sense such electrical signals via any bipolar combination of electrodes 40, 42, 44A-44D, 48, 50, 58, 62, 66, and 67. Furthermore, any of the electrodes 40, 42, 44A-44D, 48, 50, 58, 62, 66, and 67 may be used for unipolar sensing in combination with housing electrode 58.

In some examples, IMD 16 delivers pacing pulses via bipolar combinations of electrodes 40, 42, 44A-44D, 48 and 50 to produce depolarization of cardiac tissue of heart 12. In some examples, IMD 16 delivers pacing pulses via any of electrodes 40, 42, 44A-44D, 48 and 50 in combination with housing electrode 58 in a unipolar configuration. For example, electrodes 40, 42, and/or 58 may be used to deliver RV pacing to heart 12. Additionally or alternatively, electrodes 44A-44D and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 66 and 67, and housing electrode 58. Electrodes 58, 62, and 66 may also be used to deliver cardioversion pulses to heart 12. Electrodes 62, 66 and 67 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36.

Two or more electrodes, and the polarity of the electrodes, define a vector, or path, for delivering pacing pulses to heart 12. As described above, there are numerous vectors that may be used to deliver pacing pulses to heart 12. For example, various combinations of the electrodes on a single quadripolar lead, i.e., a lead with four electrodes on the lead, such as lead 20, as well as combinations of the lead electrodes with an electrode on the housing of an IMD may provide sixteen different vectors that may be used to deliver pacing pulses to a chamber of heart 12 that the lead is within or on.

Similarly, two or more electrodes define a vector, or path, for sensing signals from heart 12 or more generally from patient 14.

Figure 3:
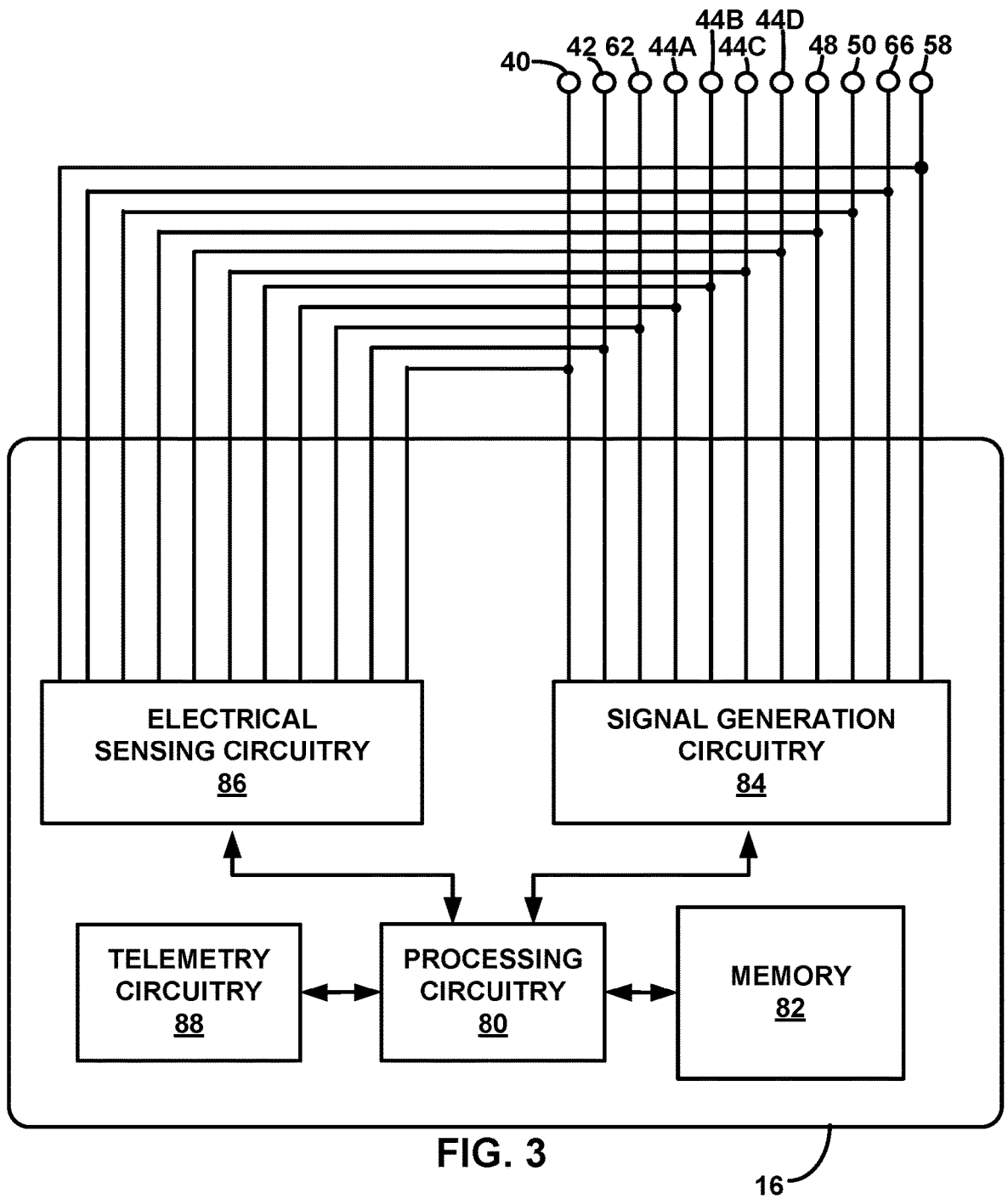
FIG. 3 is a block diagram illustrating an example configuration of an implantable medical device.

FIG. 3 is a block diagram illustrating one example configuration of IMD 16. In the example illustrated by FIG. 3, IMD 16 includes a processing circuitry 80, memory 82, signal generation circuitry 84, electrical sensing circuitry 86, and telemetry circuitry 88. Memory 82 may include computer-readable instructions that, when executed by processing circuitry 80, cause IMD 16 and processing circuitry 80 to perform various functions attributed throughout this disclosure to IMD 16, or processing circuitry 80. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The example techniques described in this disclosure may be performed by processing circuitry of an IC chip. One example of the IC chip includes processing circuitry 80, parts of signal generation circuitry 84, parts of electrical sensing circuitry 86, and parts of telemetry circuitry 88. For example, the IC chip may include components such as switches and other electrical components that can be formed inside of the IC chip. However, some components of signal generating circuitry 84, sensing circuitry 86, and telemetry circuitry 88 may be external to the IC chip, such as components that are too large to be formed within the IC chip. The components external to the IC chip may be formed on a printed circuit board (PCB) and coupled to the IC chip forming a so-called "hybrid circuit."

In this disclosure, the term "circuitry" is used to generically refer to the combination of various components. As an example, circuitry includes processing circuitry 80, signal generation circuitry 84, electrical sensing circuitry 86, and telemetry circuitry 88. All or some of the circuitry may be part of the IC chip. For instance, the IC chip may include the circuitry which includes processing circuitry 80, the parts of signal generating circuitry 84 that are formed within the IC chip, and parts of electrical sensing circuitry 86 that are formed within the IC chip. In this disclosure, when techniques are described as being performed by circuitry such techniques may be performed by a combination of processing circuitry 80, signal generation circuitry 84, and/or sensing circuitry 86.

In some examples, it may be possible for the circuitry to be spread across a plurality of IC chips. The techniques described in this disclosure should not be considered limited to the example a single IC chip includes all components of the circuitry. Other combinations of components illustrated in FIG. 3 in one or more IC chips is possible, and the techniques described in this disclosure are applicable to such different configurations of components in one or more IC chips.

Processing circuitry 80 may include any one or more of a microprocessor, a controller, a digital signal processor (DSP), an application specific integrated circuit (ASIC), a field-programmable gate array (FPGA), or equivalent discrete or integrated logic circuitry. In some examples, processing circuitry 80 may include multiple components, such as any combination of one or more microprocessors, one or more controllers, one or more DSPs, one or more ASICs, or one or more FPGAs, as well as other discrete or integrated logic circuitry. The functions attributed to processing circuitry 80 herein may be embodied as software, firmware, hardware or any combination thereof.

Processing circuitry 80 controls signal generation circuitry 84 to deliver stimulation therapy, e.g., cardiac pacing or CRT, to heart 12 according to a selected one or more therapy programs, which may be stored in memory 82. Signal generation circuitry 84 is electrically coupled to electrodes 40, 42, 44A-44D, 48, 50, 58, 62, and 66, via conductors of the respective lead 18, 20, 22, or, in the case of housing electrode 58, via an electrical conductor disposed within housing 60 of IMD 16. For example, elements of signal generation circuitry 84 implemented in the IC chip may include a plurality of therapy pins through which the therapy pulses travel. These therapy pins (or simply pins) are electrical connections to which conductors on respective lead 18, 20, 22 connect as the way for current to flow out of electrodes of respective lead 18, 20, 22 and back to the ground potential of IMD 16.

Signal generation circuitry 84 is configured to generate and deliver electrical stimulation therapy to heart 12 via selected combinations of electrodes 40, 42, 44A-44D, 48, 50, 58, 62, and 66. In some examples, signal generation circuitry 84 is configured to delivery cardiac pacing pulses. In other examples, signal generation circuitry 84 may deliver pacing or other types of stimulation in the form of other signals, such as sine waves, square waves, or other substantially continuous time signals.

Stimulation generation circuitry 84 may include a switch circuitry (e.g., switches illustrated in FIG. 4) and processing circuitry 80 may use the switch circuitry to select, e.g., via a data/address bus, which of the available electrodes are used to deliver pacing pulses. Processing circuitry 80 may also control which of electrodes 40, 42, 44A-44D, 48, 50, 58, 62, and 66 is coupled to signal generation circuitry 84 for generating stimulus pulses, e.g., via the switch circuitry. The switch circuitry may include a switch array, switch matrix, multiplexer, or any other type of switching device suitable to selectively couple a signal to selected electrodes. The example analog circuit illustrated in FIG. 4 may be part of the switch circuitry of signal generation circuitry 84, or may be separate from the switch circuitry.

Electrical sensing circuitry 86 monitors signals from at least one of electrodes 40, 42, 44A-44D, 48, 50, 58, 62, or 66 in order to monitor electrical activity of heart 12. Electrical sensing circuitry 86 may also include a switch circuitry to select which of the available electrodes are used to sense the cardiac activity. In some examples, processing circuitry 80 selects the electrodes that function as sense electrodes, or the sensing vector, via the switch circuitry within electrical sensing circuitry 86.

Electrical sensing circuitry 86 includes multiple detection channels, each of which may be selectively coupled to respective combinations of electrodes 40, 42, 44A-44D, 48, 50, 58, 62, or 66 to detect electrical activity of a particular chamber of heart 12. Each detection channel may comprise an amplifier that outputs an indication to processing circuitry 80 in response to detection of an event, such as a depolarization, in the respective chamber of heart 12. In this manner, processing circuitry 80 may detect the occurrence of R-waves and P-waves in the various chambers of heart 12.

Memory 82 stores intervals, counters, or other data used by processing circuitry 80 to control the delivery of pacing pulses by signal generation circuitry 84. Such data may include intervals and counters used by processing circuitry 80 to control the delivery pacing pulses to one or both of the left and right ventricles for CRT. The intervals and/or counters are, in some examples, used by processing circuitry 80 to control the timing of delivery of pacing pulses relative to an intrinsic or paced event, e.g., in another chamber.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide data to be uplinked to external device 24 and receive data from external device 24 via telemetry circuitry 88.

The circuitry such as processing circuitry 80 and portions of signal generation circuitry 84 within the IC chip, and portions of signal generation circuitry 84 external to the IC chip may be configurable to delivery therapy in accordance with a plurality of vectors. Prior to implantation, when forming the circuit board (e.g., PCB) that houses the IC chip that includes processing circuitry 80 and signal generation circuitry 84, a technician or manufacturing device may populate components such as capacitors that connect to the pins of the IC chip and are used for therapy delivery. Example of such capacitors include hold capacitors and tip capacitors for supporting atrial, right ventricular, and four left ventricular "canodes." There may also be a support hold capacitor and support channel that can pace through any of the other three chambers.

Any electrode that couples to a tip capacitor is a cathode, any electrode that provides the pacing return path to ground is an anode. For example, a bipolar RV pace has RVTIP as cathode and RVRING as anode. The LV electrodes couple to both a tip capacitor and a ground return path, so they can be configured as anode or cathode, thus the term "canoed." A canode is configured as an anode or cathode, but not bath simultaneously.

The hold and tip capacitors, as well as other components, may be too large to be housed inside the IC chip that includes processing circuitry 80 and/or portions of signal generation circuitry 84. Accordingly, the IC chip includes pins to connect circuitry within the IC chip to the hold and tip capacitors, or other components external to the IC chip.

If determined (e.g., by a physician) that there may be a subset of vectors via which IMD 16 does not need to deliver therapy or sense signals, then the technician or manufacturing device may not include these external components on the substrate (e.g., printed wring board (PWB) or PCB) that couple to pins that would have been used to deliver therapy in accordance with the subset of vectors that are not needed. The substrate (e.g., PWB or PCB) provides a mounting point and connectivity between the ICs and external components. Depopulation refers to removing external components or not including external components for unused channels (e.g., unused vectors) and modifications to the control logic, as described in this disclosure, for those channels. As an example of depopulation, for some devices, none of the LV components would be populated, such as when no LV lead is used in IMD 16 (e.g., for a single or dual chamber system).

As described above, the depopulation of external components for pins of unused vectors or possibly even if the external components are coupled to the pins of unused vectors can cause the pins of the unused vectors to be in an electrically floating state and couple noise. Accordingly, processing circuitry 80 may selectively close switches in signal generation circuitry 84 so that the pins of unused vectors are fixed to a set voltage level.

Prior to implantation or subsequent to implantation, processing circuitry 80 may be configured to determine that one or more pins, for therapy delivery in accordance with a first subset of vectors of a plurality of vectors, are in an electrically floating state. One example way in which processing circuitry 80 may perform such determination is based on register values stored in a register. The register may be part of processing circuitry 80 or memory 82.

In one example, the register values may indicate which configurations are available (e.g., Quadripolar, CRT, DR, VR). Each of these configurations may be associated with one or more vectors. In one example, the register values may indicate which vectors (e.g., channels) are available (e.g., A, LVT, LVR1, LVR2, LVR3). The terms available, populated, and active are all used interchangeably to indicate vectors that can be used to deliver therapy or sense signals. The terms unavailable, depopulated, and inactive are all used interchangeably to indicate vectors that may not be used to delivery therapy or sense signals.

Figure 4:
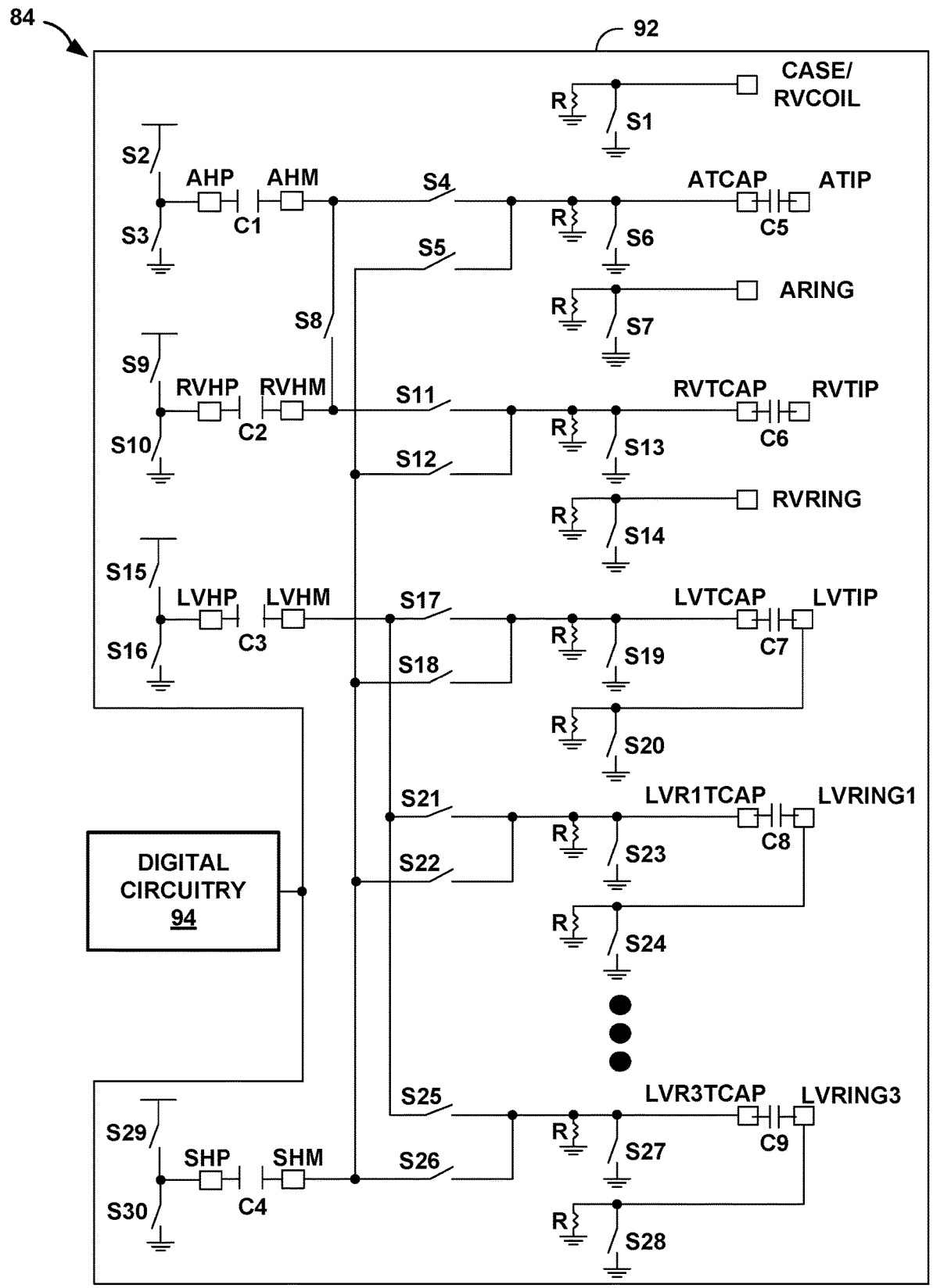
FIG. 4 is a block diagram illustrating an example of a signal generation circuitry shown in FIG. 3 in greater detail.

The reset state of the register is that all channels (e.g., vectors) are available/populated, but this should be written by firmware as part of writing the manufacturing trim values. Those values are stored in non-volatile memory 82 and are written as part of the reset routine. The concept is that for a single chamber device, it resets to all vectors available. Firmware then writes the configuration register with the stored manufacturing trim value and configures the switch matrix (e.g., as illustrated in FIG. 4) to reflect the depopulated channels.

Table 1 below provides example register names and values used for indicating which subset of vectors are available and which subset of vectors are not available. In one example, although other ways are possible, after reset, IMD 16 may be set for full configuration (e.g., all vectors are available), and processing circuitry 80 may then remove vectors until the subset of vectors that are available remain. The decision may be made to use configuration implementation with unlock key (e.g., the register stores a password, and for configuring IMD 16, the password is needed).

The example provided in Table 1 is merely one example and should not be considered limiting. Also, the example values stored in the register are one example of how values may be stored and their corresponding functions.

TABLE 1

| Register Control | |
|---|---|
| Register Name | Description |
| PO_depop<br>7:3-Unlock plus reserved bits<br>2-A_dp<br><br>1-LV_dp<br><br>0-LVQ_dp | Reset Value: 0x0011<br>Writing a 1 to a bit field sets that configuration to depop mode, which grounds the tip and ring paths for that channel as well as the corresponding hold capacitor cap positive and negative pads. Writing a 1 to an LV channel grounds the corresponding tip and ring of that canode pair. if LV and LVQ configurations are high, then the LV Hold cap positive and negative pads are also grounded. |

Accordingly, processing circuitry 80 may determine the first subset of vectors (e.g., those that IMD 16 is not to deliver) based on one or more stored register values. Processing circuitry 80 may selectively close switches within signal generation circuitry 84 based on the determined first subset of vectors. The stored register values comprise one of a predetermined set of register values, each of the set of register values indicating a respective configuration of IMD 16, and each configuration enabling a respective subset of the plurality of vectors.

There may be other ways to determine which pins are populated and which pins are depopulated. As one example, processing circuitry 80 may determine which pins are populated and which pins are depopulated based on impedance checks. Depopulated pins may measure at a higher impedance than populated pins. Other types of determining which pins are populated and which pins are depopulated may be possible.

FIG. 4 is a block diagram illustrating an example of a signal generation circuitry shown in FIG. 3 in greater detail. For instance, FIG. 4 illustrates that signal generation circuitry 84 includes analog circuitry 92 and digital circuitry 94. In some examples, digital circuitry 94 may be part of the processing circuitry 80, or may not be included in examples where the functionality of digital circuitry 94 is performed using various other techniques. It should be understood that sensing circuitry 86 may share components with signal generation circuitry 84. Accordingly, although FIG. 4 is described with respect to stimulation therapy, the various pins illustrated in FIG. 4 may be used to form sensing vectors as well.

Analog circuitry 92 illustrates the various pins of the IC chip that can used to delivery therapy or sense signals in accordance with various vectors. The various pins of stimulation generation circuitry 84 includes the AHP (where HP stands for hold capacitor plus), AHM (where HM stands for hold capacitor minus), ATCAP, ATIP, ARING, RVHP, RVHM, RVTCAP, RVTIP, RVRING, LVHP, LVHM, LVT-CAP, LVTIP, LVR1TCAP, LVRING1, LVR2TCAP (not shown), LVRING2 (not shown), LVR3TCAP, LVRING3, SHP, and SHM.

As an example of a stimulation vector, a stimulation signal that flows from the ATIP pin through heart 12 and back to the ARING pin would form one vector. Another stimulation vector may be a stimulation signal that flows from the ATIP pin through heart 12 and back to the case. In general, a vector is formed when the stimulation signal flows form a "TIP" pin and returns through a "RING" pin or case. For the LV vectors, a pin may function as TIP or RING (e.g., canoed). In this way, there may be a plurality of vectors with which IMD 16 may deliver therapy, and similarly, there may be a plurality of vectors with which IMD 16 senses signals (e.g., where sensing signals includes receiving the signals, rather than outputting signals).

The capacitors C1-C9 may be external to the IC chip that includes other portions of signal generation circuitry 84. Each of these capacitors may be too large to be formed within the IC chip, and therefore, the various pins are used to couple other circuitry of signal generation circuitry 84 to the external capacitors C1-C9.

As an example, to deliver therapy to the atrium through one bipolar atrial vector, processing circuitry 80 may close the S2 to charge hold capacitor C1. Capacitor C1 is an external capacitor and coupled to the AHP and AHM pins of the IC chip. Then to deliver the pulse, processing circuitry 80 may cause discharge of the pulse through capacitor C5 coupled to pins ATCAP and ATIP, through heart 14, and back through the ARING pin and ground via switch S7. Therapy delivery via the other vectors may operate in a similar manner and may be configurable via the various switches.

However, not all of capacitors C1-C9 may be populated in all examples. For instance, if particular pins are not coupled to electrodes, then capacitors coupled to the corresponding pins used for therapy delivery or sensing in accordance with that vector may be depopulated (e.g., removed or not placed). For a depopulated channel (e.g., vector), all of the pins left floating by the removal of components should be controlled. For instance, for a depopulated vector, the tip and ring pads may be connected to a set voltage level (e.g., supply voltage VSS or a ground potential) through the example switches illustrated in FIG. 4. The LV nodes (e.g., pins of LV) may also control the electrode side of the tip capacitor, and depopulated LV tip capacitors should be connected to a set voltage level (e.g., supply voltage VSS or a ground potential).

For instance, switches S6, S13, S19, S23, and S27 may couple respective pins for the tip pads and respective CAP pads to the ground potential, and switches S1, S7, S14, S20, S24, and S8 may couple respective pins for the ring pads to the ground potential. Although the various pins are illustrated as being coupled to the ground potential, it may be possible for one or more of the pins to be coupled to the supply voltage or to some other fixed voltage level.

Also, if the hold capacitor for a vector is depopulated (e.g., if one or more of C1, C2, C3, or C4 is depopulated), then the respective HP and HM pins should be coupled to a set voltage level (e.g., supply voltage or the ground potential, and the ground potential is illustrated) via switches S3, S10, S16 and S30. In some examples, the RV is always populated, and therefore only switches S3 and S16 would be needed to couple to the ground potential. Furthermore, as these vectors are not in use, processing circuitry 80 may be configured to set the amplitude for these vectors equal to 0 to effectively disable the vectors.

In examples where sensing circuitry 86 shares the various components illustrated in FIG. 4 with signal generation circuitry 84, it may be possible that some of the pins are not used for therapy delivery but are used for sensing purposes. In such examples, the tip capacitors between the TIP and RING may be populated, but the hold capacitors are depopulated. The HP and HM pins in such examples should be coupled to a set voltage level, as would be floating.

In this manner, processing circuitry 80, which may be configurable to deliver therapy or sense signals in accordance with a plurality of vectors, may determine that one or more pins for therapy delivery or sensing in accordance with a first subset of vectors of the plurality of vectors are in an electrically floating state, and may selectively close one or more switches to couple at least a subset of the one or more pins to one or more set voltage levels. For example, processing circuitry 80 may selectively close a switch of the one or more switches to couple a pin of the one or more pins to a ground potential. The pins for therapy delivery or sensing in accordance with the first subset of vectors are not coupled to components external to the chip that includes signal generation circuitry 84 and the pins for therapy delivery or sensing in accordance with the first subset of vectors.

Processing circuitry 80 may then cause signal generation circuitry 84 to deliver therapy (or sense) in accordance with a vector of a second subset of vectors. For instance, signal generation circuitry 84 may deliver therapy via one or more pins for therapy delivery in accordance with the vector of the second subset of vectors. The one or more pins for therapy delivery in accordance with the vector of the second subset of vectors are different than the one or more pins for therapy delivery or sensing in accordance with the first subset of vectors. The one or more pins for therapy delivery in accordance with the vector of the second subset of vectors are not in the electrically floating state prior to therapy delivery or subsequent to therapy delivery.

In some examples, signal generation circuitry 84 may not deliver therapy until determined that a valid therapy path exists. However, the closing of one or more switches for pins for therapy delivery or sensing in accordance with the first subset of vectors may potentially cause a false positive that a valid therapy path exists. For example, processing circuitry 80 may determine that a valid therapy path exists if at least one of the ring pins is connected to the ground potential, which may occur if one of the ring pins used for the first subset of vectors is coupled to the ground potential.

As an example, assume that therapy is to be delivered only through RVTIP/RVRING. Therefore, ARING is coupled to the ground potential via the S7 switch. In this example, the closing of the S7 switch forms a feedback signal to processing circuitry 80 indicating that a ring pin is connected to ground. However, in this case, because ARING is not coupled to any external components, there may not be an actual valid therapy path.

Accordingly, in some examples, processing circuitry 80 may not cause signal generation circuitry 84 to delivery therapy or signal generation circuitry 84 may not be configured to delivery therapy until after determined that at least at one pin, other than the one or more pins for therapy delivery in accordance with the first subset of vectors, is coupled to a ground potential. For example, if assumed that switch S7 is a first switch and ARING is a first pin, the circuitry (e.g., one or both of processing circuitry 80 and portions of signal generation circuitry 84 such as digital circuitry 94) may determine that at least a second switch couples a second pin to the ground potential, where the second pin is usable for therapy delivery in accordance with at least one of the second subset of vectors. In general, the circuitry may avoid delivery of therapy after the first switch (e.g. S7) couples the first pin (e.g., ARING) to the ground potential until determined that at least the second switch couples the second pin to the ground potential, and may deliver therapy only after determined that at least the second switch couples the second pin to the ground potential.

As an example implementation, a pace cannot occur unless there is a valid anode path (i.e., ground). The pacing capacitor may be coupled to the tip electrode until a return path has been activated. The programming (e.g., processing circuitry 80) sets up a return path for a pace. For instance, a bipolar RV pace should activate only the RV Ring path for return. If that switch does not activate, no pace will occur. However, if there is another return path, such as Case, then the pace will be delivered. For the single chamber device, if the A and LV paths are depopulated and those pads are coupled to ground, the circuitry (e.g., digital circuitry 94) does not allow those to report a valid ground path, so only closing the RVring or Case provides an actual anode return path.

Digital circuitry 94 may be configured to mask the feedback signal from a pin, used for the first subset of vectors, being coupled to the ground potential so that signal generation circuitry 84 only delivers therapy when a valid therapy path is present. As digital circuitry 94 is part of the portion of signal generation circuitry 84, the generic term "circuitry" also includes digital circuitry 94.

In some examples, rather than using digital circuitry 94, processing circuitry 80 may be configured with firmware or software that evaluates which switches are providing the feedback signal of coupling to ground, and ensuring that there is at least a ring pin connection to ground for ring pins used in the second subset of vectors based on the evaluation of which switches provided feedback signal of coupling to ground. Other techniques to ensure that a pin used for the second subset of vectors is coupled to ground may be possible.

One way for digital circuitry 94 to determine that at least one pin used for the second subset of vectors is coupled to the around potential is to compare a signal that causes the first switch (e.g., S7) to couple the first pin (e.g., ARING) to the ground potential to a signal that indicates that one or more switches are to couple one or more pins that are used to deliver therapy in accordance with at least one vector of the second subset of vectors to the ground potential. Digital circuitry 94 may determine that at least one switch used to deliver therapy in accordance with at least one vector of the second subset of vectors is coupled to the ground potential based on the comparison.

Figure 5:
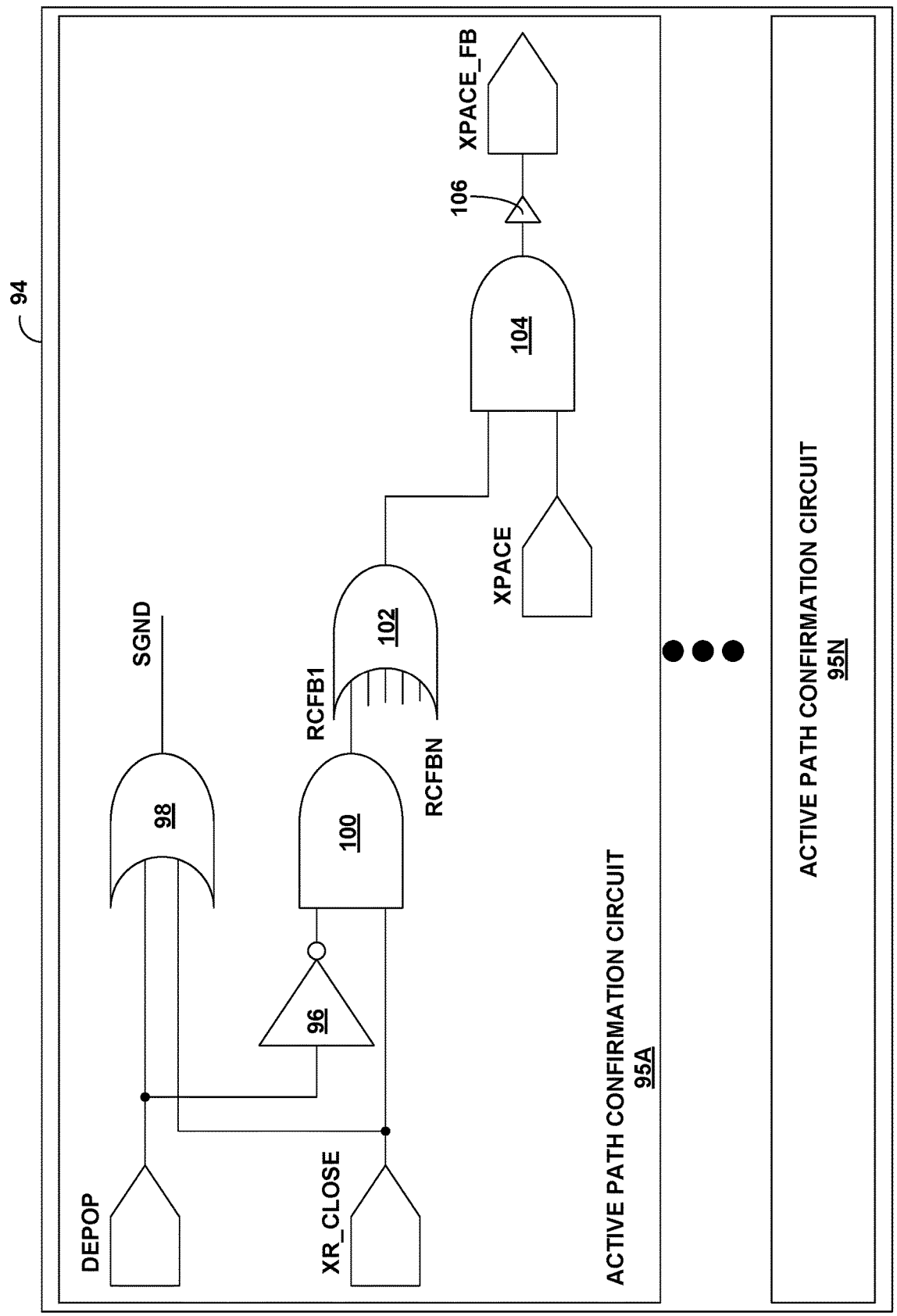
FIG. 5 is block diagram illustrating an example of digital circuitry shown in FIG. 4 in greater detail.

FIG. 5 is block diagram illustrating an example of digital circuitry 94 shown in FIG. 4 in greater detail. As illustrated, digital circuitry 94 includes a plurality of active path confirmation circuits 95A-95N. Each one of the active path confirmation circuits 95A-95N may correspond to a respective channel (e.g., vector) of analog circuitry 92. For example, active path confirmation circuit 95A may be for ATCAP/ARING vector, active path confirmation circuit 95B may be for RVTCAP/RVRING vector, and so forth.

Active path confirmation circuit 95A includes OR gate 98 that receives as input signal values DEPOP and XR_CLOSE and compares these signal values. DEPOP is the signal generated by processing circuitry 80 based on the determination of whether a vector is needed or not (e.g., whether the vector is active or inactive). For instance, active path confirmation circuit 95A may correspond to ATCAP/ARING. In this example, if ATCAP/ARING is not needed, and the external components of ATCAP/ARING are depopulated, then the DEPOP signal for active path confirmation circuit 95A may be a logic high. The XR_CLOSE signal indicates whether that specific vector is going to be used for delivering pacing therapy. For instance, XR_CLOSE set the return (anode) path. It also goes to the circuit that eventually gates the pacing signal XPACE.

OR gate 98 compares the DEPOP signal and the XR_CLOSE signals and generates a logic high or logic low based on the comparison. OR gate 98 performs the OR function of the DEPOP and XR_CLOSE signal. Assume that ATCAP/ARING vector is inactive and depopulated. In this example, the DEPOP will be a logic high. Although the XR_CLOSE signal should be a logic high, in accordance with the OR function, regardless of whether XR_CLOSE is a logic high or a logic low, if DEPOP is at a logic high, the output of OR gate 98 will be a logic high causing switch S7 to close coupling ARING to the ground potential.

As also illustrated in FIG. 5, active path confirmation circuit 95A includes inverter 96 that inverts the value of DEPOP (e.g., the output of inverter 96 is !DEPOP). AND gate 100 receives the XR_CLOSE signal and the !DEPOP signal and compares these signals to perform the AND function. Keeping with the example where active path confirmation circuit 95A is for A vector (e.g., ATCAP/ARING), which is depopulated, then the output of inverter 96 is a logic low. Accordingly, regardless of whether XR_CLOSE is a logic high or a logic low, the output of AND gate 100 will be a logic low because !DEPOP is a logic low, which is because DEPOP is a logic high. The output of AND gate 100 is RCFB1.

As illustrated, OR gate 102 receives the RCFB1 signal. OR gate 102 also receives the RCFB2-RCFBN signals from respective ones of active path confirmation circuit 95B-95N. Each of the RCFB signals indicate whether the anode pins (e.g., ring or case), with which their active path confirmation circuits 95 are associated, are coupled to the ground potential.

However, because RCFB1 is from active path confirmation circuit 95, which is associated with a depopulated vector, the value of RCFB1 should be set to a logical zero even if ARING is coupled to the ground potential. This way the coupling of ARING to the ground potential is masked from signal generation circuitry 84 or processing circuitry 80 as a valid therapy path.

As described above, the output of OR gate 98 is a logic high, which causes the ARING pin to be coupled to the ground potential by closing the S7 switch. If the ARING pin were not depopulated, then RCFB1 signal should indicate that the ARING pin is coupled to ground. However, because the ARING pin is depopulated, the RCFB1 signal should not indicate that the ARING pin is coupled to ground to ensure that the ARING pin is not determined to be a valid therapy path. With the example circuit illustrated in FIG. 5, the RCFB1 output indicates that the ARING pin is not coupled to ground even though the ARING pin is coupled to ground.

OR gate 102 compares the RCFB1-RCFBN signals, performs the OR function, and outputs a logic high if at least one of RCFB1-RCFBN is at a logic high. AND gate 104 receives the output from OR gate 102, and compares the output to XPACE, which is a signal that indicates that pacing therapy is to be delivered via the vector for which active path confirmation circuit 95A is associated. If both the output of OR gate 102 is high and XPACE is high, then the XPACE_FB signal is delivered indicating that pacing therapy can commence, with driver 106 providing gain if needed.

The operations of OR gate 102 and AND gate 104 may be understood in the context of the operation of two or more of active path confirmation circuits 95A-95N. For instance, assume that active path confirmation circuit 95A is associated with A vector (e.g., ATCAP/ARING) as per above example, and assume that active path confirmation circuit 95B is associated with RV vector (e.g., RVTCAP/RVRING). In this example, external components such as capacitor C6 are populated for the RV vector, and external components such as capacitor C5 are depopulated for the A vector.

As above, the DEPOP signal for A vector in active path confirmation circuit 95A is a logic high because the A vector is depopulated. This means that RCFB1 is a logic low, and switch S7 is closed and couples ARING to the ground potential.

For active path confirmation circuit 95B, the DEPOP signal for the RV vector is a logic low because the RV vector is populated. Also, the XR_CLOSE signal for RV vector in active path confirmation circuit 95B is a logic high. Therefore, OR gate 98 of active path confirmation circuit 95B receives a logic low for DEPOP and a logic high for XR_CLOSE, meaning that the output for OR gate 98 of active path confirmation circuit 95B is a logic high, which closes switch S14 and couples RVRING to the ground potential.

The output of inverter 96 of active path confirmation circuit 95B is a logic high because the DEPOP signal for active path confirmation circuit 95 is a logic low. Also, XR_CLOSE is a logic high for active path confirmation circuit 95B. Accordingly, the output of AND gate 100 of active path confirmation circuit 95B is a logic high. Assume that the output of AND gate 100 of active path confirmation circuit 95B is RCFB2.

OR gate 102 of active path confirmation circuit 95B receives RCFB1 from active path confirmation circuit 95A and receives RCFB2. As described above, even though ARING pin is coupled to the ground potential via switch S7, RCFB1 is set to a logic low. Therefore, OR gate 102 of active path confirmation circuit 95B may not output a logic high solely based on RCFB1. However, OR gate 102 of active path confirmation circuit 95B may output a logic high based on RCFB2 being a logic high. In this way, the output of OR gate 102 is not a logic high until at least one anode pin for a populated vector is coupled to the ground potential. It is insufficient for the ARING pin to be coupled to the ground potential for OR gate 102 of active path confirmation circuit 95B to output a logic high indicating that the pacing therapy can be delivered. When RCFB2 is a logic high (or RCFB from another vector that is populated is a logic high), then OR gate 102 of active path confirmation circuit 95B outputs a logic high.

AND gate 104 of active path confirmation circuit 95B receives the logic high from OR gate 102 of active path confirmation circuit 95B and the logic high from XPACE (meaning that pacing therapy is to be delivered via the RV vector). AND gate 104 outputs a logic high that XPACE_FB outputs indicating that the pacing therapy can be delivered.

In the example illustrated in FIG. 5, to mask the feedback that a ring pin for a depopulated vector is coupled to a ground potential additional control signals may be needed. Table 2 provides an example listing of control signals. All of these control signals are not needed in every example and more control signals may exist. Note that A_DV_ENA and LV_DV_ENA map to the corresponding hold cap to VSS control signals in the analog block. Paces or amplitude writes (other than 0V) to a depopulated channel should be ignored. Signals below assume that in CRT mode the LV vectors are tip to ring and ring to tip.

TABLE 2

Control Signals

| PO_Depop signal | xTIP signal (controlled by depop signal in analog) | xRing signal (cntlrd by depop signal in analog) | xHP signal (cntlrd in digital sea) | xHM signal controlled in digital sea) |
|---|---|---|---|---|
| A_dp_dh | ATCAP_RCHG_CLOSE_dh | AR_CLOSE_dh | A_DV_ENA_dh | N_AHM_TO_VSS_dh |
| DEPOP_LV_dp_dh | LVTCAP_RCHG_CLOSE_dh, LVR1TCAP_RCHG_CLOSE_dh | LVT_CL OSE_dh, LVR1_C LOSE_dh | LV_DV_ENA_dh (if all LV depop signals are active) | N_LVHM_TO_VSS_dh (if all LV depop signals are active) |
| DEPOP_LV Q_dp_dh | LVR2TCAP_RCHG_CLOSE_dh, LVR3TCAP_RCHG_CLOSE_dh | LVR2_C LOSE_dh, LVR3_C LOSE_dh | LV_DV_ENA_dh (if all LV depop signals are active) | |

Moreover, for a device configured as RV Single chamber, the depopulation control is written so as to control the A and LV floating nodes external to the IC chip. Processing circuitry 80 may determine the configuration, so processing circuitry 80 does not allow pacing vectors other than RV bipolar or unipolar. In the same way, when external device 24 queries the device, IMD 16 may only report back the capabilities for the populated channels, in this case, RV unipolar/bipolar. External device 24 may only display those choices.

Figure 6:
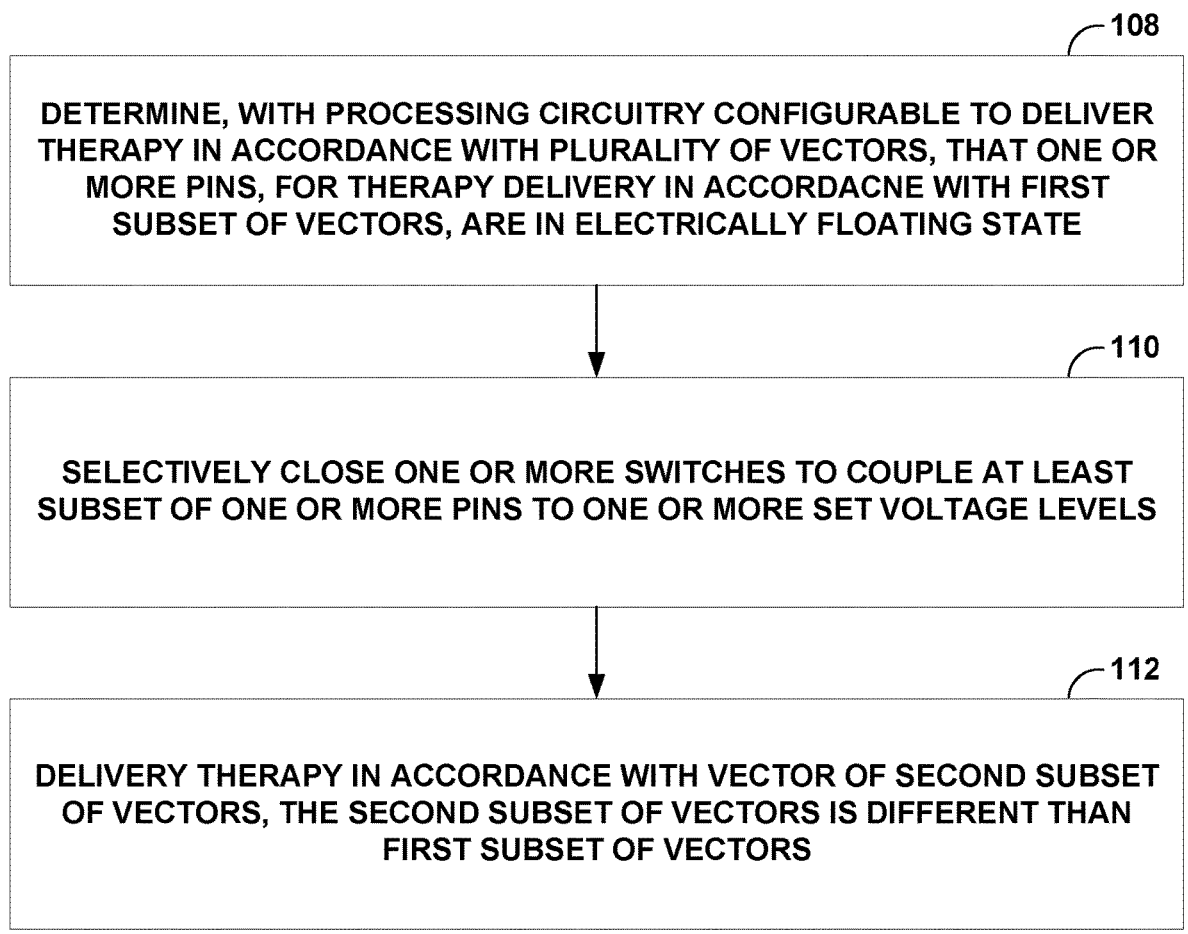
FIG. 6 is a flow diagram illustrating an example method of configuring pacing circuitry of an implantable medical device in accordance with one or more examples described in this disclosure.

FIG. 6 is a flow diagram illustrating an example method of configuring pacing circuitry of an implantable medical device in accordance with one or more examples described in this disclosure. Circuitry (e.g., one or combination of processing circuitry 80 and portions of signal generation circuitry 84 within the IC chip) that is configurable to control delivery of therapy in accordance with a plurality of vectors that one or more pins for therapy delivery or sensing in accordance with a first subset of vectors are in an electrically floating state (108). As one example, the circuitry (e.g., via processing circuitry 80) may determine the first subset of vectors based on one or more stored register values. The stored register values may include one of a predetermined set of register values, each of the set of register values indicating a respective configuration of IMD 16, and each configuration enabling a respective subset of the plurality of vectors. The pins for therapy delivery or sensing in accordance with the first subset of vectors may not be coupled to components external to the IC chip that includes processing circuitry 80 and the pins for therapy delivery or sensing in accordance with the first subset of vectors.

The circuitry (e.g., via processing circuitry 80) may selectively close one or more switches (e.g., switches S1-S30) to couple at least a subset of the one or more pins to one or more set voltage levels (110). For instance, the circuitry may close a switch of the one or more switches to couple a pin of the one or more pins to a ground potential. The circuitry may selectively close the one or more switches to couple at least the subset of the one or more pins to respective set voltage levels without coupling the one or more pins to respective set voltage levels via components external to the IC chip. In other words, in some examples, external components may not be needed to couple pins for inactive vectors to a set voltage level; however, the techniques described in this disclosure should not be construed to require that no external components are used to couple pins for inactive vectors to one or more set voltage levels.

The circuitry may cause IMD 16 to deliver therapy (or sensing) in accordance with a vector of a second subset of vectors, where the second subset of vectors is different than the first subset of vectors (112). For instance, the circuitry may cause IMD 16 to deliver therapy or sense signals via one or more pins for therapy delivery in accordance with the vector of the second subset of vectors, where the one or more pins for therapy delivery or sensing in accordance with the vector of the second subset of vectors are different than the one or more pins for therapy delivery or sensing in accordance with the first subset of vectors. Also, the one or more pins for therapy delivery or sensing in accordance with the vector of the second subset of vectors may not be in the electrically floating state prior to therapy delivery or subsequent to therapy delivery.

In some examples, pacing therapy may not be delivered until confirmation that a valid therapy path exists. For instance, the circuitry (e.g., via digital circuitry 92 of signal generation circuitry 84) may determine that at least one pin, other than the one or more pins for therapy delivery in accordance with the first subset of vectors, is coupled to a ground potential. In such examples, the circuitry (e.g., via processing circuitry 80) may cause IMD 16 to deliver therapy in accordance with the vector of the second subset of vectors of the plurality of vectors after determining that the at least one pin, other than the one or more pins for therapy delivery in accordance with the first subset of vectors, is coupled to the ground potential.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit or circuit for purposes of clarity, it should be understood that the techniques of this disclosure may be performed by a combination of circuitry.

While particular combinations of various aspects of the techniques are described above, these combinations are provided merely to illustrate examples of the techniques described in this disclosure. Accordingly, the techniques of this disclosure should not be limited to these example combinations and may encompass any conceivable combination of the various aspects of the techniques described in this disclosure.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media. In this manner, computer-readable media generally may correspond to a tangible computer-readable storage media which is non-transitory. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other structure suitable for implementation of the techniques described herein. The techniques could be fully implemented in one or more circuits or logic elements.

The techniques of this disclosure may be implemented in a wide variety of devices or apparatuses, including a medical device, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the claims.

The invention claimed is:

1. A method of configuring cardiac pacing circuitry of an implantable medical device, the method comprising:
   determining, with circuitry that is configurable to control delivery of therapy or sense signals in accordance with a plurality of vectors, that one or more pins, for therapy delivery or sensing in accordance with a first subset of vectors of the plurality of vectors, are in an electrically floating state;
   selectively closing one or more switches to couple at least a subset of the one or more pins to one or more set voltage levels; and
   delivering therapy in accordance with a vector of a second subset of vectors of the plurality of vectors, wherein the second subset of vectors is different than the first subset of vectors.

2. The method of claim 1, further comprising:
   determining that at least one pin, other than the one or more pins for therapy delivery in accordance with the first subset of vectors, is coupled to a ground potential,
   wherein delivering therapy comprises delivering therapy in accordance with the vector of the second subset of vectors of the plurality of vectors after determining that the at least one pin, other than the one or more pins for therapy delivery in accordance with the first subset of vectors, is coupled to the ground potential.

3. The method of claim 1, wherein selectively closing one or more switches comprises closing a switch of the one or more switches to couple a pin of the one or more pins to a ground potential.

4. The method of claim 3, wherein the switch comprises a first switch, and the pin comprises a first pin, the method further comprising:
   determining that at least a second switch couples a second pin to the ground potential, wherein the second pin is usable for therapy delivery in accordance with at least one of the second subset of vectors, and
   wherein delivering therapy comprises delivering therapy based on the determination that at least the second switch couples the second pin to the ground potential.

5. The method of claim 4, wherein delivering therapy based on the determination that at least the second switch couples the second pin to the ground potential comprises:
   avoiding delivery of therapy after the first switch couples the first pin to the ground potential until determined that at least the second switch couples the second pin to the ground potential; and
   delivering therapy only after determined that at least the second switch couples the second pin to the ground potential.

6. The method of claim 4, wherein the one or more switches comprises a first set of one or more switches, and wherein determining that at least a second switch couples a second pin to the ground potential comprises:
comparing a signal that causes the first switch to couple the first pin to the ground potential to a signal that indicates that a second set of one or more switches are to couple one or more pins that are used to deliver therapy in accordance with at least one vector of the second subset of vectors to the ground potential; and
determining that at least the second switch couples the second pin to the ground potential based at least in part on the comparison.

7. The method of claim 1, further comprising:
determining the first subset of vectors based on a stored register value,
wherein selectively closing one or more switches comprises selectively closing the one or more switches based on the determined first subset of vectors.

8. The method of claim 7, wherein the stored register value comprises one of a predetermined set of register values, each of the set of register values indicating a respective configuration of the implantable medical device, and each configuration enabling a respective subset of the plurality of vectors.

9. The method of claim 1, wherein an integrated circuit (IC) chip includes the processing circuitry, and wherein the IC chip includes the one or more switches.

10. The method of claim 9, wherein selectively closing one or more switches comprises selectively closing the one or more switches to couple at least the subset of the one or more pins to respective set voltage levels without coupling the one or more pins to respective set voltage levels via components external to the IC chip.

11. The method of claim 1, wherein delivering therapy comprises delivering therapy via one or more pins for therapy delivery in accordance with the vector of the second subset of vectors, wherein the one or more pins for therapy delivery in accordance with the vector of the second subset of vectors are different than the one or more pins for therapy delivery in accordance with the first subset of vectors.

12. The method of claim 11, wherein the one or more pins for therapy delivery in accordance with the vector of the second subset of vectors are not in the electrically floating state prior to therapy delivery or subsequent to therapy delivery.

13. The method claim 1, wherein the pins for therapy delivery in accordance with the first subset of vectors are not coupled to components external to an integrated circuit (IC) chip that includes the processing circuitry and the pins for therapy delivery in accordance with the first subset of vectors.

14. The method of claim 1, wherein the second subset of vectors comprises a sensing vector, the method further comprising sensing one or more signals via the sensing vector.

15. An implantable medical device (IMD), the device comprising:
an integrated circuit (IC) chip comprising:
a plurality of switches; and
a plurality of pins;
circuitry that is configurable to control delivery of therapy or sense signals in accordance with a plurality of vectors, wherein the circuitry is configured to:
determine that one or more pins of the plurality of pins, for therapy delivery or sensing in accordance with a first subset of vectors of the plurality of vectors, are in an electrically floating state;
selectively close one or more switches of the plurality of switches to couple at least a subset of the one or more pins to one or more set voltage levels; and
cause the IMD to deliver therapy in accordance with a vector of a second subset of vectors of the plurality of vectors, wherein the second subset of vectors is different than the first subset of vectors.

16. The device of claim 15, wherein the IC chip includes the circuitry.

17. The device of claim 15, wherein the circuitry is configured to determine that at least one pin, other than the one or more pins for therapy delivery in accordance with the first subset of vectors, is coupled to a ground potential, and wherein to cause the IMD to deliver therapy, the processing circuit is configured to cause the IMD to deliver therapy in accordance with the vector of the second subset of vectors of the plurality of vectors after determining that the at least one pin, other than the one or more pins for therapy delivery in accordance with the first subset of vectors, is coupled to the ground potential.

18. The device of claim 15, wherein to selectively close one or more switches, the circuitry is configured to close a switch of the one or more switches to couple a pin of the one or more pins to a ground potential.

19. The device of claim 18, wherein the switch comprises a first switch, and the pin comprises a first pin, wherein the circuitry is configured to:
determine that at least a second switch couples a second pin to the ground potential, wherein the second pin is usable for therapy delivery in accordance with at least one of the second subset of vectors, and
wherein to cause the IMD to deliver therapy, the circuitry is configured to cause the IMD to deliver therapy based on the determination that at least the second switch couples the second pin to the ground potential.

20. The device of claim 19, wherein to cause the IMD to deliver therapy based on the determination that at least the second switch couples the second pin to the ground potential, the circuitry is configured to:
avoid causing the IMD to deliver therapy after the first switch couples the first pin to the ground potential until determined that at least the second switch couples the second pin to the ground potential; and
cause the IMD to deliver therapy only after determined that at least the second switch couples the second pin to the ground potential.

21. The device of claim 19, wherein the one or more switches comprises a first set of one or more switches, and wherein to determine that at least a second switch couples a second pin to the ground potential, the circuitry is configured to:
compare a signal that causes the first switch to couple the first pin to the ground potential to a signal that indicates that a second set of one or more switches are to couple one or more pins that are used to deliver therapy in accordance with at least one vector of the second subset of vectors to the ground potential; and
determine that at least the second switch couples the second pin to the ground potential based at least in part on the comparison.

22. The device of claim 15, wherein the circuitry is configured to determine the first subset of vectors based on a stored register value, wherein to selectively close one or more switches, the circuitry is configured to selectively close the one or more switches based on the determined first subset of vectors.

23. The device of claim 22, wherein the stored register value comprises one of a predetermined set of register values, each of the set of register values indicating a respective configuration of the implantable medical device, and each configuration enabling a respective subset of the plurality of vectors.

24. The device of claim 15, wherein to selectively close one or more switches, the circuitry is configured to selectively close the one or more switches to couple at least the subset of the one or more pins to respective set voltage levels without coupling the one or more pins to respective set voltage levels via components external to the IC chip.

25. The device of claim 15, wherein to cause the IMD to deliver therapy, the circuitry is configured to cause the IMD to deliver therapy via one or more pins for therapy delivery in accordance with the vector of the second subset of vectors, wherein the one or more pins for therapy delivery in accordance with the vector of the second subset of vectors are different than the one or more pins for therapy delivery in accordance with the first subset of vectors.

26. The device of claim 25, wherein the one or more pins for therapy delivery in accordance with the vector of the second subset of vectors are not in the electrically floating state prior to therapy delivery or subsequent to therapy delivery.

27. The device of claim 15, wherein the pins for therapy delivery in accordance with the first subset of vectors are not coupled to components external to the IC chip that includes the circuitry and the pins for therapy delivery in accordance with the first subset of vectors.

28. The device of claim 15, wherein one or more pins of the plurality of pins used for therapy delivery in accordance with the second subset of vectors are coupled to at least one of:
one or more electrodes on one or more leads coupled to the IMD; or
one or more capacitors that are external to the IC chip.

29. A computer-readable storage medium storing instruction thereon that when executed cause circuitry that is configurable to control delivery of therapy or sense signals in accordance with a plurality of vectors to:
determine that one or more pins, for therapy delivery or sensing in accordance with a first subset of vectors of the plurality of vectors, are in an electrically floating state;
selectively close one or more switches to couple at least a subset of the one or more pins to one or more set voltage levels; and
cause delivery of therapy in accordance with a vector of a second subset of vectors of the plurality of vectors, wherein the second subset of vectors is different than the first subset of vectors.

* * * * *